United States Patent
Kochevar et al.

(10) Patent No.: US 7,331,350 B2
(45) Date of Patent: Feb. 19, 2008

(54) PHOTOCHEMICAL TISSUE BONDING (75) Inventors: Irene E. Kochevar, Charlestown, MA (US); Robert W. Redmond, West Newton, MA (US); Dimitri Azar, Brookline, MA (US)

(73) Assignee: The General Hospital Corporation, Boston, MA (US)

( * ) Notice: Subject to any disclaimer, the term of this patent is extended or adjusted under 35 U.S.C. 154(b) by 45 days.

(21) Appl. No.: 09/781,577

(22) Filed: Feb. 12, 2001

(65) Prior Publication Data

US 2002/0022606 A1 Feb. 21, 2002

Related U.S. Application Data (60) Provisional application No. 60/181,980, filed on Feb. 11, 2000.

(51) Int. Cl.
*A61B 19/00* (2006.01)
(52) U.S. Cl. .................. 128/898; 606/213
(58) Field of Classification Search ............... 128/898; 522/13; 606/213–221
See application file for complete search history.

(56) References Cited

U.S. PATENT DOCUMENTS

| | | | |
|---|---|---|---|
| 4,127,109 A | 11/1978 | Fourney et al. | |
| 5,147,514 A | 9/1992 | Mechanic | 204/157.68 |
| 5,209,776 A | 5/1993 | Bass et al. | |
| 5,292,362 A | 3/1994 | Bass et al. | |
| 5,374,515 A | 12/1994 | Parenteau et al. | |
| 5,431,790 A | 7/1995 | Nesburn et al. | 204/157.68 |
| 5,552,452 A * | 9/1996 | Khadem et al. | 522/63 |
| 5,565,551 A | 10/1996 | Lewis et al. | 530/405 |
| 5,571,216 A | 11/1996 | Anderson | |
| 5,616,562 A | 4/1997 | Murphy et al. | |
| 5,829,448 A | 11/1998 | Fisher et al. | 128/898 |
| 5,844,016 A | 12/1998 | Sawhney et al. | |
| 5,917,045 A | 6/1999 | Lewis et al. | 546/100 |
| 5,942,534 A | 8/1999 | Trauner et al. | 514/410 |
| 6,030,974 A | 2/2000 | Swartz et al. | |
| 6,107,466 A | 8/2000 | Hasan et al. | 530/351 |

FOREIGN PATENT DOCUMENTS

WO WO 91/04073 4/1991

OTHER PUBLICATIONS

Judy et al. "Heat- free photochemical tissue welding with 1,8-naphthalimide" 1993, SPIE Proceedings vol. 1876 pp. 17-18, http://www.spie.org/web/abstracts/1800/1876.html.*
Saunders "Tissue Welding A new kind of laser surgery uses molecules to stitch together wounds" Jan. 19, 1998, pp. 16-17, Science News: Biology, http://www.discover.com/science_news/bioscience.html.*

(Continued)

*Primary Examiner*—Tom Barrett
(74) *Attorney, Agent, or Firm*—Edwards Angell Palmer & Dodge LLP; Amy M. Leahy (57) ABSTRACT

Photochemical tissue bonding methods include the application of a photosensitizer to a tissue, e.g., cornea, followed by irradiation with electromagnetic energy to produce a tissue seal. The methods are useful for wound repair, or other tissue repair.

23 Claims, 5 Drawing Sheets

OTHER PUBLICATIONS

Abergel et al., "Skin closure by Nd: YAG laser welding", May 1986, J Am Acad Dermatol. 14: 810-814.

Aveline et al., "Photochemistry of the Nonspecific Hydroxyl Radical Generator, N-Hydroxypyridine-2(1H)-thione",Oct. 23, 1996, J. Am Chem Soc 118:10113-10123.

Barton et al., "The Generation and Reactivity of Oxygen . . . ", Jan. 1991 Tetrahedron Lett 32:311-314.

Boivin et al., "N-Hydroxy—2-Pyridnethione: A Mild . . . ",Nov. 1990 Tetrahedron Lett 31:6869-6872.

Chuck et al., "Dye-Enhanced Laser Tissue Welding", Lasers in Surgery and Medicine 9:471-477 (1989).

Cilesiz et al., "Controlled Temperature Tissue Fusion . . . ", (1997) Lasers Surg Med 21:269-86.

Diestelhorst et al., "Clinical Dose-Regimen with Latanoprost, . . . ", Survey of Ophthalmology, vol. 41, Supp. 2, Feb. 1997:s77-s81.

Gandin et al., "Quantum Yield of Singlet Oxygen . . . ", Mar. 1983 Photochem Photobiol 37:271-278).

Goins et al., "Photodynamic biologic tissue glue to enhance . . . ", J Cataract Refract Surg., vol. 23, Nov. 1997:1331-1338.

Goins et al., "Relative strength of photodynamic . . . ", J Cataract Refract Surg., vol. 24, Dec. 1998:1566-1570.

Gollnick & Schenck , "Mechanism and Stereoselectivity of . . . ", (1964) Pure Appl Chem 9:507-525.

Henrick et al., "Organic tissue glue in the closure of cataract incisions", Sep. 1987 J Cataract Refract Surg 13:551-553.

Henrick et al., "Organic tissue glue in the closure of cataract incisions in rabbit eyes", Sep. 1991 J Cataract Refract Surg 17:551-555).

Judy et al., "Gel electrophoretic studies of photochemical . . . ", (1994) Proc SPIE—Int Soc Opt Eng 2128:506-509.

Katol et al., "Aggregation of Collagen Exposerd to UVA . . . ", Photochemistry and Photobiology, vol. 59, No. 3, pp. 343-349, 1994.

Khadem et al., "Photodynamic Biologic Tissue Glue", Cornea, vol. 13, No. 5, (1994):406-410.

Khodadoust, "Tissue Adhesives in Ophthalmology", Surgical Pharmacology of the Eye (1985):223-234.

Massicotte et al., "Effects of Endogenous Absorption in Human . . . " (1998) Lasers in Surgery and Medicine 23:18-24.

Melki et al., "Photochemical Tissue Repair (Welding) of Clear Cornea Incisions", Mar. 1999 IVOS, vol. 40, No. 4:s340, abstract 1803-B711.

Mulroy et al., "Photochemical Tissue Bonding for Corneal Repair and Transplants", 27th Annual Meetingf of the American Society for Photobiology, Abstract MPM-E21 (1999).

Oz et al., "Tissue soldering by use of indocyanine . . . ", J Vascular Surgery, vol. 11, No. 5, (1990):718-25.

Poppas et al., "Temperature-Controlled Laser . . . ", (1996) Lasers in Surgery and Medicine 18:335-344.

Poppas et al., "Human Albumin Solder Supplemented . . . ", (1996) Lasers in Surgery and Medicine 19: 360-368.

Ramshaw et al., "Methylene blue sensitized . . . ", Biochimica et Biophysica Acta 1206 (1994)225-230.

Shigemitsu et al., "The utilization of a biological adhesives for wound . . . ", (1997) International Ophthalmology 20:323-328.

Spoerl et al., "Induction of Cross-links in Corneal Tissue", Exp. Eye Res.(1998) 66, 97-103.

Stewart et al., "Laser Assisted Vascular . . . ", (1996) Lasers in Surgery and Medicine19:9-16.

Timberlake et al., Corneal Laser Welding Using A Light-Activated Protein-Crosslinking Dye, Investigation Ophthalmology & Visual Science 38(4) S510, Mar. 15, 1997.

Wider et al., "Skin Closure with Dye-Enhanced . . . ", Dec. 1991 Plastic Reconstr Surg 88:1018-1025).

Toriumi D.S., et al. (1990) "Histotoxicity of cyanoacrylate tissue adhesives. A comparative study." Arch. Otololaryngol. Head Neck Surg. 116: 546-550.

Fujita T., et al. (2000) "Successful preservation of human skin by vitrification." J. Burn Care Rehabit. 21: 304-309.

Forseth D.M., et al. (1992) "The current status of cyanoacrylate and fibrin tissue adhesives" J. Long Term Eff. Med. Implants 2(4): 221-233.

Bass & Treat (1995) "Laser Tissue Welding: A comprehensive review of current and future clinical applications" Lasers Surg. Med. 17: 315-349.

Dahlstrom K.K., et al. (1991) "The use of Autologous Fibrin Adhesive in Skin Trasportation" Plastic and Reconstructive Surgery 89(5): 968-972.

L. Mulroy et al. "Photochemical Keratodesmos for Repair or Lamellar Corneal Incisions" Investigative Ophthalmology & Visual Science, Oct. 2000, vol. 41, No. 11, pp. 3335-3340.

Lemp MA. Report of the National Eye Institute/Industry Workshop on Clinical Trials in dry eyes. CLAO J. (1995) 21: 221-232.

Musa OM, Choi SY, Horner JH, Newcomb M., Absolute Rate Constants for alpha-Amide Radical Reactions. J Org Chem. Feb. 6, 1998;63(3):786-793.

Al-Maharik N. Engman L, Malmstrom J, Schiesser Ch., J Org Chem Sep. 21, 2001;66(19):6286-90.

Chaulk SG, Pezacki JP, MacMillan AM., Biochemistry Aug. 29, 2000;39(34):10448-53.

Aveline BM, Redmond RW., Photochem Photobiol Sep 1998;68(3):266-75.

Epe B, Ballmaier D, Adam W, Grimm GN, Saha-Moller CR, Nucleic Acids Res May 1, 1996;24(9):1625-31.

Reszka KJ, Chignell CF., Photochem Photobiol Nov. 1994;60(5):450-4.

Lepri E, Castagnino E, Binaglia L., Giampietri A, Corsano S, Fioretti MC., Arzneimittelforschung Mar. 1993;43(3):381-3.

Mulroy L, Kim J, Wu I, Scharper P, Melki SA, Azar DT, Redmond RW, Kochevar IE., Invest Ophthalmol Vis Sci Oct. 2000;41(11):3335-40.

Khadem J, Troung T, Ernest JT., Cornea Sep. 1994;13(5):406-10.

Manning FJ, Wehrly SR, Foulks GN., Ophthalmology Dec. 1995; 102(12): 1953-1957.

Tabery HM, Acta Ophthalmol Scand Apr. 1998; 76(2): 142-145.

Kim J., Foulks GN, Cornea May 1999; 18(3): 328-332.

Arch Ophthalmol Jul. 1992; 110(7): 984-993.

Tseng SC, Zhang SH, Cornea Jul. 1995; 14(4): 427-435.

Wander AH, Neumeister RD, Tschismadia I, Choromokos EA, Madukawa T., Cornea 1985-1986; 4(1) 8-13.

Nom MS., Acta Ophthalmol (Copenh) 1967; 45(3): 347-358.

http://www.oftalmored.com/ojoseco/cap26.htm.

http://www.medal.org/docs_ch19/doc_ch19.10.html.

Prause JU Kriegbaum NJ et al. Rose Bengal Score- A possible key parameter when evaluating disease level and progression in Primary Sjogren's Syndrome. J. Autoimmunity 1989; 2: 501-507.

Van Bijsterveld OP. Diagnostic tests in the Sicca Syndrome. Arch Ophthal. 1969; 82:10-14.

Judy, M.M., J. Matthews, R. Boriack, A. Burlacu, D. Lewis, R. Utecht. "Heat-free phtotchemical tissue welding with 1, 8-naphthalimide dyes using visible (420nm) light", SPIE vol. 1876: 175-179.

Judy M.M., L. Chen, L. Fuh, H. Nosir, R. Jackson, J. Matthews, D. Lewis, R. Utecht, D. Yuan. "Photochemical cross-linking of type 1 collagen with hydrophobic and hydrophyilic 1, 8 naphthalimide dyes. " SPIE. vol. 2682: 53-55.

Hoekstra, A. H. Struszcyk, O. Kivekas. "Percutaneous microcrystilline chitosan application for sealing arterial puncture sites." Biomaterials, 19:1467-1471, 1998.

Riley J. N., T. Dickson, D. Hou, P. Rogers, K. March, K. McNally-Heintzzelman. "Improved laser-assisted vascular tissue fusion using light-activated surgical adhesive in a porcine model." Biomed Sci Instrum. 37:451-6, 2001.

Moser, D., J. Riley, B. Sorg. A. Welch, K. McNally Heintzellman. "New range of light-activated surgical adhesives for tissue repair." Biomed Sci Instruments: 37:441-449, 2001.

U. Kumar, D. Albala. "Newer techniques in intracorporeal tissue approximation: suturing, tissue adhesives, and microclips." Urol Clin North Am. 28 (1): 15-21, 2001.

McNally, K., B. Sorg. A. Welch, "Novel solid protein soldier designs for laser-assisted tissue repair". Lasers Surg Med. 27(2): 147-157, 2000.

Bleustein, C., C Walker, D. Felsen, D. Poppas. "Semi-solid albumin soldier improved mechanical properties for laser tissue welding." *Lasers Surg Med.* 27(2): 140-146, 2000.

Sorg, B., K. McNally, A. Welch. Biodegradable polymer film reinforcement of an indocyanine green-doped liquid albumin soldier for laser-assisted incision closure. *Lasers Surg Med.* 27(1): 73-81, 2000.

McNally, K., B. Sorg, E. Chan, A. Welch, J. Dawes, E. Owen. "Optimal parameters for laser tissue soldiering: II. Premixed versus separate dye-soldier techniques." Lasers Surg Med. 26(4): 346-356, 2000.

Tanaka, T., S. Furutani, M. Nakamura, T. Nishida. "Changes in extracellular matrix components after excimer laser photoablation in rat cornea." *Jpn J Opthalmol.* 43(5): 348-354, 1999.

Lauto, A., I. Kerman, M. Ohebshalon, D. Felsen, D. Poppas. "Two-layer film as a laser soldiering bi+2omaterial," *Lasers Surg Med.* 25(3): 250-256, 1999.

G. Timberlake, A. Patmore, A. Shallal, D. McHugh, and J. Marshall, "Thermal and infrated diode laser effects on indocyamine green treated corneal collagen," presented at the SPIE annual meeting, Jan. 19, 1993, paper 1882-28.

Quinn, James, et al. "A Randomized Trial Comparing Octylcyanoacrylate Tissue Adhesive and Sutures in the Management of Lacerations," *JAMA.* 277 # 19: 1527-1530, May 1997.

Oz, Mehhmet, et al. "Comparison of laser-assisted fibrinogen-bonded and sutured canine arteriovenous anastomoses," *Surgery.* 112 #1: 76-83, Jul. 1992.

Campion, Edmund, et al. "Repair of Peripheral Nerves with the Argon Laser," *The Journal of Bone and Joint Surgery.* vol. 72-A #5: 715-723, Jun. 1990.

Kuo, Paul. "Tissue Fusion," *Laser in Maxillofacial Surgery and Dentistry.* 175-178.

Donkerwolcke, M., et al. "Tissues and Bone Adhesives- Historical Aspects," *Biomaterials.* 19: 1461-1466, 1998.

Bingley, John, et al. "Late Complications of Tissue Glues in Aortic Surgery," *Ann Thorac Surg.* 69: 1764-1768, 2000.

Tang, J., et al. "Original Articles Morphological Analysis of Microarterial Media Repair After 830 nm Diode Laser Assisted End to end Anastomosis: Comparison with Conventional Manual Suture," *Lasers in Medical Science.* 12: 300-305, 1997.

Detweiler, Mark, et al. "Sutureless and Reduced Suture Anastomosis of Hollow Vessels With Fibrin Glue: A Review," *Journal of Investigative Surgery.* 12: 245-262, 1999.

Dunn, Christopher, et al. "Fibrin Sealant: A Review of its Use in Surgery and Endoscopy," *Drugs.* 58 #5: 863-886, Nov. 1999.

Wider, Todd, et al. "Skin Closure with Dye-Enhanced Laser Welding and Fibrinogen," *Plastic and Reconstructive Surgery.* 88 #6: 1018-1025, Dec. 1991.

Bernard, Laurie, et al. "A Prospective Comparison of Octyl Cyanoacrylate Tissue Adhesive (Dermabond) and Suture for the Closure of Excisional Wounds in Children and Adolescents," *Arch Dermatol.* 137: 1177-1180, Sep. 2001.

Gelli, R., et al. "Vessel Wall Recovery After Diode Laser Assisted Microvascular Anastomosis: Clinical and Histologic analysis and Long Term Follow Up," *Journal of Reconstructive Microsurgery.* 13 #3: 199-205, Apr. 1997.

Oz, Mebment, et al. "Indocyanine Green Dye Enhanced Welding with a Diode Laser," *Surgical Forum: Vascular Surgery.* 316-319.

Bass, Lawrence, et al. "Changes in Type 1 Collagen Following Laser Welding," *Lasers in Surgery and Medicine.* 12: 500-505, 1992.

Bailes, Julian, et al. "Review of Tissue Welding Applications in Neurosurgery," *Microsurgery.* 8: 242-244, 1987.

\* cited by examiner

PHOTOCHEMICAL TISSUE BONDING

CROSS-REFERENCE TO RELATED APPLICATIONS

This application claims priority to U.S. Provisional Application Ser. No. 60/181,980, filed Feb. 11, 2000, the contents of which are incorporated herein by reference.

BACKGROUND

Traditional wound closure methods, such as staples and sutures, have numerous drawbacks, including the possible occurrence of inflammation, irritation, infection, wound gape, and leakage. In corneal applications, sutures often produce astigmatism due to uneven suture tension. The cosmetic results of the use of staples and sutures can also be undesirable.

Possible alternatives to sutures include hemostatic adhesives, such as fibrin sealants (Henrick et al. (1987) *J Cataract Refract Surg* 13:551-553; Henrick et al. (1991) *J Cataract Refract Surg* 17:551-555), cyanoacrylate adhesives (Shigemitsu et al. (1997) *International Ophthalmology* 20:323-328), and photodynamic tissue glue, composed of a mixture of riboflavin-5-phosphate and fibrinogen, which has been reported to close cataract incisions and attach donor cornea in corneal transplants (Goins et al. (1997) *J Cataract Refract Surg* 23:1331-1338; Goins et al. (1998) *J Cataract Refract Surg* 24:1566-1570; U.S. Pat. No. 5,552,452). In addition, temperature-controlled tissue welding has been attempted in bovine cornea and rat intestine (Barak et al. (1997) *Surv Ophthalmol* 42 Supp.1:S77-81; Cilesiz et al. (1997) *Lasers Surg Med* 21:269-86). Photochemical tissue welding of dura mater has also been reported, using 1,8 naphthalimides irradiated with visible light (Judy et al. (1993) *Proc. SPIE-Int. Soc. Opt. Eng.* 1876:175-179).

The ideal technique for wound closure would be simpler, more rapid, and prone to fewer post operative complications than conventional techniques. In the cornea, an ideal tissue repair or wound closure technique would produce a water-tight seal without inducing astigmatism.

SUMMARY

The present invention is based, in part, on the discovery that the application of a photosensitizer, e.g., Rose Bengal (RB), riboflavin-5-phosphate (R-5-P), methylene blue (MB), or N-hydroxypyridine-2-(1H)-thione (N-HTP), to a tissue, e.g., cornea, skin, tendon, cartilage, or bone, followed by photoactivation, e.g., irradiation with electromagnetic energy, e.g., light, can produce a tissue-tissue seal (e.g., to repair a wound, or seal a tissue transplant) without collagen denaturation or heat induced peripheral tissue damage. Furthermore, the tissue-tissue seal can be produced when the photosensitizer is applied to the tissue in the absence of an exogenously supplied source of cross-linkable substrate, e.g., protein, e.g., fibrin or fibrinogen, or protein-based tissue adhesive or glue. Such exogenous substances are often suggested to be used to contribute cross-linkable protein to a tissue. (A graft tissue is not considered a source of exogenously supplied cross-linkable substrate.) This procedure is referred to herein as photochemical tissue bonding (PTB). PTB can be used ex vivo or in vivo in a subject, e.g., a human, or a non-human animal, preferably a non-albino animal.

Accordingly, in one aspect, the invention features, a method for cross-linking tissue, e.g., creating a tissue seal. The method includes identifying a tissue in need of repair, e.g., a collagenous tissue, e.g., cornea, skin, bone, cartilage, or tendon; contacting the tissue, and optionally a second tissue, with at least one photosensitizer agent, e.g., Rose Bengal (RB), riboflavin-5-phosphate (R-5-P), methylene blue (MB), or N-hydroxypyridine-2-(1H)-thione (N-HTP), to form a tissue-photosensitizer mixture; and applying electromagnetic energy, e.g., light, to the tissue-photosensitizer mixture sufficient to produce cross linking of a protein, e.g., collagen, in the tissue. The tissue is not contacted with an exogenously supplied source of cross-linkable substrate, e.g., protein, e.g., fibrin or fibrinogen, or protein-based tissue adhesive or glue, which is cross linked by the application of electromagnetic energy.

In a preferred embodiment, the tissue is corneal tissue. E.g., one or more elements, e.g., cut or otherwise separated edges or surfaces, of the subject's corneal tissue can be joined together, or to graft tissue.

In a preferred embodiment, the tissue is in need of repair. For example, the tissue, e.g., cornea, has been subjected to trauma, a surgical incision, LASIK flap reattachment, corneal transplant, or correction of astigmatism.

In a preferred embodiment, the photosensitizer agent is selected from the group consisting of Rose Bengal, riboflavin-5-phosphate, methylene blue, and N-hydroxypyridine-2-(1H)-thione.

In a preferred embodiment, the photosensitizer agent is Rose Bengal.

In a preferred embodiment, the contacting step occurs ex vivo.

In a preferred embodiment, the contacting step occurs in vivo in a subject, e.g., a human, or an non-human animal, preferably a non-albino animal, e.g., a non-albino rabbit.

In a preferred embodiment, the subject is other than an albino animal, e.g., other than an albino rabbit.

In a preferred embodiment, the subject is a human.

In a preferred embodiment, the application of electromagnetic energy to the tissue-photosensitizer mixture occurs without substantial thermal tissue damage, e.g., without shrinkage or deformation around the wound site.

In a preferred embodiment, the application of electromagnetic energy to the tissue-photosensitizer mixture occurs without more than a 3° C. rise in temperature as measured, e.g., with an imaging thermal camera during irradiation.

In a preferred embodiment, the application of electromagnetic energy to the tissue-photosensitizer mixture occurs without more than a 2° C. rise in temperature as measured, e.g., with an imaging thermal camera during irradiation.

In a preferred embodiment, the application of electromagnetic energy to the tissue-photosensitizer mixture occurs without more than a 1° C. rise in temperature as measured, e.g., during irradiation with an imaging thermal camera.

In another aspect, the invention features, a method for repairing a corneal lesion, e.g., a corneal incision, laceration, or a corneal transplant, in a subject, e.g., a human, or a non-human animal, preferably a non-albino animal. The method includes: contacting a corneal tissue with at least one photosensitizer agent, e.g., RB, R-5-P, MB, or N-HTP, and applying electromagnetic energy, e.g., light, to the corneal tissue-photosensitizer mixture sufficient to produce a reactive species, e.g., a reactive oxygen species, from the photosensitizer. The corneal tissue is not contacted with an exogenously supplied source of cross-linkable substrate, e.g., protein, e.g., fibrin or fibrinogen, or protein-based tissue adhesive or glue, which is cross-linked by the application of electromagnetic energy.

In a preferred embodiment, the corneal lesion is caused by a surgical procedure.

In a preferred embodiment, the surgical procedure is selected from the group consisting of corneal transplant surgery, cataract surgery, laser surgery, keratoplasty, penetrating keratoplasty, posterior lamellar keratoplasty, LASIK, refractive surgery, cornea reshaping, and treatment of corneal laceration.

In a preferred embodiment one or more elements, e.g., cut or otherwise separated edges or surfaces, of the subject's corneal tissue can be joined together, or to graft tissue.

In a preferred embodiment, a subject's muscle tendon can be joined to the subject's eye. E.g., an ocular misalignment can be reduced, adjusted, or corrected, e.g., by joining an eye muscle tendon to the eye.

In another preferred embodiment, the cornea is in need of correction for astigmatism. For example, PTB can be used to correct, reduce, or decrease astigmatism, e.g., by inducing astigmatism in the orthogonal meridian, thereby counteracting preexisting astigmatism. In a preferred embodiment, PTB induces a predictable degree of corrective astigmatism.

In a preferred embodiment, the method further comprises administration of an adjunctive therapy, e.g., contact lens therapy, amniotic membrane therapy, LASIK therapy, or administration of antibiotics.

In a preferred embodiment, the electromagnetic energy applied is greater than 1200 $J/cm^2$. In another preferred embodiment, the electromagnetic energy applied is between 200 and 1200 $J/cm^2$. In another preferred embodiment, the electromagnetic energy applied is between 200 and 800 $J/cm^2$. In yet another preferred embodiment, the electromagnetic energy applied is between 200 and 500 $J/cm^2$. In yet another preferred embodiment, the electromagnetic energy applied is between 300 and 600 $J/cm^2$. In another preferred embodiment, the electromagnetic energy applied is between 350 and 550 $J/cm^2$.

In a preferred embodiment, the electromagnetic energy is applied at an irradiance less than 3.5 $W/cm^2$.

In a preferred embodiment, the subject is other than an albino animal, e.g., other than an albino rabbit.

In another aspect, the invention features, a method for repairing a corneal lesion in vivo in a living subject, e.g., a human, or a non-human animal, preferably a non-albino animal. The method includes contacting a corneal tissue with Rose Bengal (RB) to form a corneal tissue-RB mixture; and applying electromagnetic energy, e.g., light, to the corneal tissue-RB mixture in a manner effective to elicit the production of a reactive species, e.g., a reactive oxygen species, from the RB. The corneal tissue is not contacted with an exogenously supplied source of cross-linkable substrate, e.g., protein, e.g., fibrin or fibrinogen, or protein-based tissue adhesive or glue, which is cross-linked by the application of electromagnetic energy.

In a preferred embodiment, the subject is a human.

In a preferred embodiment, the corneal lesion is caused by a surgical procedure.

In a preferred embodiment, the surgical procedure is selected from the group consisting of corneal transplant surgery, cataract surgery, laser surgery, keratoplasty, penetrating keratoplasty, posterior lamellar keratoplasty, LASIK, refractive surgery, cornea reshaping, and treatment of corneal laceration.

In a preferred embodiment one or more elements, e.g., cut or otherwise separated edges or surfaces, of the subject's corneal tissue can be joined together, or to graft tissue.

In a preferred embodiment, a subject's muscle tendon can be joined to the subject's eye. E.g., an ocular misalignment can be reduced, adjusted, or corrected, e.g., by joining an eye muscle tendon to the eye.

In another preferred embodiment, the cornea is in need of correction for astigmatism. For example, PTB can be used to correct, reduce, or decrease astigmatism, e.g., by inducing astigmatism in the orthogonal meridian, thereby counteracting preexisting astigmatism. In a preferred embodiment, PTB induces a predictable degree of corrective astigmatism.

In a preferred embodiment, the method further comprises administration of an adjunctive therapy, e.g., contact lens therapy, amniotic membrane therapy, LASIK therapy, or administration of antibiotics.

In a preferred embodiment, the subject is other than an albino animal, e.g., other than an albino rabbit.

In another aspect, the invention features a kit for repairing corneal lesions, which kit includes a photosensitizer agent, e.g., RB, R-5-P, MB, or N-HTP, and instructions for photoactivation of the photosensitizer agent to repair the corneal lesion.

In a preferred embodiment the kit does not include a source of cross-linkable substrate, e.g., protein, e.g., fibrin or fibrinogen, or protein-based tissue adhesive or glue, for use with the photosensitizer.

In a preferred embodiment, the photosensitizer agent is Rose Bengal.

The details of one or more embodiments of the invention are set forth in the accompanying drawings and the description below.

Other features, objects, and advantages of the invention will be apparent from the description and drawings, and from the claims.

DETAILED DESCRIPTION

Photochemical tissue bonding (PTB), as described herein, provides a method to create a tissue-tissue seal, e.g., to treat a wound, e.g., a corneal wound, without collagen denaturation or heat-induced peripheral tissue damage. PTB, as described herein, involves the application of a photosensitizer to a wound surface followed by photoactivation by laser irradiation to seal the wound. The photosensitizer can be effectively applied to seal a wound, or otherwise repair a tissue, in the absence of an exogenous protein-based adhesive, such as fibrinogen.

Methods of the invention provide high tensile strength repair and have no requirement for an exogenous protein, e.g., fibrinogen, that must be isolated from the patient to be treated or derived from one or more donors. Methods of the invention do not require the use of chemical glues, e.g., cyanoacrylate adhesives. The methods described herein minimize tissue thermal denaturation of proteins caused by tissue heating.

Closure of corneal wounds or corneal transplants with sutures can be associated with neo-vascularisation, rejection of the donor cornea, and induced post operative astigmatism partly due to uneven suture tension. This can occur after penetrating keratoplasty where numerous sutures are needed to hold the graft in place. Suturing techniques designed to evenly distribute tension across corneal grafts may still result in significant astigmatism. Additionally, loose or broken sutures can leave a patient vulnerable to microbial keratitis. The sutures used are skill intensive and are mainly performed by corneal specialists. The methods described herein do not require the use of sutures. Although factors such as wound healing, host graft sizing and trephination techniques also play a role in post-operative astigmatism, the methods described herein hold the graft with equally distributed force and help reduce post-operative astigmatism. PTB reduces the operating and rehabilitation time for procedures to close wounds, e.g., to treat incisions or corneal lacerations, spot seal LASIK flaps, perform cataract surgery, and attach donor cornea.

Photoactivation and Photosensitizers

The methods to create a tissue-tissue seal described herein include treating a tissue with a photosensitizer agent, e.g., RB, R-5-P, MB, or N-HTP, preferably in the absence of an exogenous protein, e.g., a protein based adhesive, e.g., fibrin or fibrinogen, and photoactivating the photosensitizer agent with electromagnetic radiation, e.g., light.

Photoactivation is used to describe the process by which energy in the form of electromagnetic radiation is absorbed by a compound, e.g., a photosensitizer, thus "exciting" the compound, which then becomes capable of converting the energy to another form of energy, preferably chemical energy. The electromagnetic radiation can include energy, e.g., light, having a wavelength in the visible range or portion of the electromagnetic spectrum, or the ultra violet and infra red regions of the spectrum. The chemical energy can be in the form of a reactive species, e.g., a reactive oxygen species, e.g., a singlet oxygen, superoxide anion, hydroxyl radical, the excited state of the photosensitizer, photosensitizer free radical or substrate free radical species. The photoactivation process described herein preferably involves insubstantial transfer of the absorbed energy into heat energy. Preferably, photoactivation occurs with a rise in temperature of less than 3 degrees Celsius (C.), more preferably a rise of less than 2 degrees C. and even more preferably, a rise in temperature of less than 1 degree C. as measured, e.g., by an imaging thermal camera that looks at the tissue during irradiation. The camera can be focused in the area of original dye deposit, e.g., the wound area, or on an area immediately adjacent the wound area, to which dye will diffuse. As used herein, a "photosensitizer" is a chemical compound that produces a biological effect upon photoactivation or a biological precursor of a compound that produces a biological effect upon photoactivation. Preferred photosensitizers are those that absorb electromagnetic energy, such as light. While not wishing to be bound by theory, the photosensitizer may act by producing an excited photosensitizer or derived species that interacts with tissue, e.g., collagenous tissue, to form a bond, e.g., a covalent bond or crosslink. Photosensitizers typically have chemical structures that include multiple conjugated rings that allow for light absorption and photoactivation. Examples of photosensitive compounds include various light-sensitive dyes and biological molecules such as, for example, xanthenes, e.g., rose bengal and erythrosin; flavins, e.g., riboflavin; thiazines, e.g., methylene blue; porphyrins and expanded porphyrins, e.g., protoporphyrin I through protoporphyrin IX, coproporphyrins, uroporphyrins, mesoporphyrins, hematoporphyrins and sapphyrins; chlorophylis, e.g., bacteriochlorophyll A, and photosensitive derivatives thereof. Preferred photosensitizers for use in the methods described herein are compounds capable of causing a photochemical reaction capable of producing a reactive intermediate when exposed to light, and which do not release a substantial amount of heat energy. Preferred photosensitizers are also water soluble. Preferred photosensitizers include Rose Bengal (RB); riboflavin-5-phosphate (R-5-P); methylene blue (MB); and N-hydroxypyridine-2-(1H)-thione (N-HTP).

Without wanting to be bound by theory, it is believed that the chemical energy, e.g., a reactive oxygen species, produced by photoactivation of the photosensitizer agent with which the tissue to be repaired is contacted, binds and causes structural changes in the amino acids of the proteins of the tissue, resulting in the formation of covalent bonds, polymerization, or cross-links between amino acids of the tissue, thus creating a proteinaceous framework that serves to seal, repair, heal, or close the tissue lesion or wound. For example, as a result of PTB treatment, strong covalent cross-links are believed to form between collagen molecules on opposing surfaces of a corneal lesion to produce a tight tissue seal.

The photosensitizer agent, e.g., RB, R-5-P, MB, or N-HTP, can be dissolved in a biocompatible buffer or solution, e.g., saline solution, and used at a concentration of from about 0.1 mM to 10 mM, preferably from about 0.5 mM to 5 mM, more preferably from about 1 mM to 3 mM.

The photosensitizer agent can be administered to the tissue by, e.g., injection into the tissue, or application onto the surface of the tissue. An amount of photosensitizer sufficient to stain, e.g., to cover the walls of, the lesion or wound to be repaired, can be applied. For example, at least 10 µl of photosensitizer solution, preferably 50 µl, 100 µl, 250 µl, 500 µl, or 1 ml, or more, of photosensitizer solution can be applied to a tissue, e.g., a cornea. Preferably, the photosensitizer has a binding efficiency, e.g., a collagen binding efficiency, such that the dye is predominantly bound to the surface of the incision.

The electromagnetic radiation, e.g., light, is applied to the tissue at an appropriate wavelength, energy, and duration, to cause the photosensitizer to undergo a reaction to affect the structure of the amino acids in the tissue, e.g., to cross-link a tissue protein, thereby creating a tissue seal. The wavelength of light can be chosen so that it corresponds to or encompasses the absorption of the photosensitizer, and reaches the area of the tissue that has been contacted with the photosensitizer, e.g., penetrates into the region where the photosensitizer is injected. The electromagnetic radiation, e.g., light, necessary to achieve photoactivation of the photosensitizer agent can have a wavelength from about 350 nm to about 800 nm, preferably from about 400 to 700 nm and can be within the visible, infra red or near ultra violet spectra. The energy can be delivered at an irradiance of about between 0.5 and 5 W/cm², preferably between about 1 and 3 W/cm². The duration of irradiation can be sufficient to allow cross linking of one or more proteins of the tissue, e.g., of a tissue collagen. For example, in corneal tissue, the duration of irradiation can be from about 30 seconds to 30 minutes, preferably from about 1 to 5 minutes. The duration of irradiation can be substantially longer in a tissue where the light has to penetrate a scattering layer to reach the wound, e.g., skin or tendon. For example, the duration of irradiation to deliver the required dose to a skin or tendon wound can be at least between one minute and two hours, preferably between 30 minutes to one hour.

Suitable sources of electromagnetic energy include commercially available lasers, lamps, light emitting diodes, or other sources of electromagnetic radiation. Light radiation can be supplied in the form of a monochromatic laser beam, e.g., an argon laser beam or diode-pumped solid state laser beam. Light can also be supplied to a non-external surface tissue through an optical fiber device, e.g., the light can be delivered by optical fibers threaded through a small gauge hypodermic needle or an arthroscope. Light can also be transmitted by percutaneous instrumentation using optical fibers or cannulated waveguides.

The choice of energy source will generally be made in conjunction with the choice of photosensitizer employed in the method. For example, an argon laser is a preferred energy source suitable for use with RB or R-5-P because these dyes are optimally excited at wavelengths corresponding to the wavelength of the radiation emitted by the argon laser. Other suitable combinations of lasers and photosensitizers will be known to those of skill in the art. Tunable dye lasers can also be used with the methods described herein.

USES

The methods described herein are suitable for use in a variety of applications, including in vitro laboratory applications, ex vivo tissue treatments, but especially in in vivo surgical procedures on living subjects, e.g., humans, and non-surgical wound healing.

The methods described herein are particularly useful for surgical applications, e.g., to seal, close, or otherwise join, two or more portions of tissue, e.g., to perform a tissue transplant operation, or to heal damaged tissue, e.g., a corneal incision. The methods described herein can be used in surgical applications where precise adhesion is necessary, and/or where the application of sutures, staples, or protein sealants is inconvenient or undesirable. For example, in corneal transplants and other eye operations, surgical complications such as inflammation, irritation, infection, wound gape, leakage, and epithelial ingrowth, often arise from the use of sutures. The photochemical tissue binding methods described herein are particularly suitable for use in surgery or microsurgery, for example, in surgical operations or maneuvers of the eye, e.g., in the repair of corneal wounds or incisions, in refractive surgery (the correction of irregularities or defects in the cornea by "shaving" an even layer off the cornea), in keratoplasty, in corneal transplants, and in correction of astigmatism, e.g., by inducing astigmatism designed to counteract preexisting astigmatism, e.g., in the orthogonal meridian.

As another example, sutures cannot be satisfactorily used on bone joint cartilage because of their mechanical interference with the mutual sliding of cartilage surfaces required for joint motion. Neither can sutures be used to seal surfaces of small blood vessels with diameters 1-2 mm or less, as sutures impinge upon the vessel lumen, compromising blood flow. Thus, the methods described herein are also useful in surgical interventions of the small vascular tissue, joint cartilage, gastro intestinal tract, nerve sheaths, small ducts (urethra, ureter, bile ducts, thoracic duct) or even the inner ear. Other procedures where sutures or staples are not indicated or desirable, and where the photochemical tissue bonding methods described herein are useful, include procedures involving laparoscopic operations or interventions such as laparoscopic (LP) thoracic procedures, LP appendectomy, LP hernia repairs, LP tubal ligations and LP orbital surgeries.

The photochemical tissue bonding methods described herein can also be used to supplement the use of sutures, e.g., to reinforce sutured anastomosis. Sutures leave a tract behind which can allow for leakage of fluids and organisms. The problem of leakage is especially critical in vascular anastomoses or for any anastomoses of a fluid-containing structure (aorta, ureter, GI tract, eye, etc.) where the fluid or contents inside can leak out through the suture hole. In one embodiment, a wound can be sutured according to general procedures and then treated with the photochemical tissue bonding methods described herein, thereby making the healing wound water tight, and impermeable to bacteria.

In addition, the methods described herein can be used in non surgical wound healing applications, e.g., a "photochemical bandage" can be used for wound healing in addition to, or in place of, a conventional bandage. In one embodiment, a biocompatible substrate, e.g., a conventional bandage material, e.g., a strip of fiber, can be impregnated with the photosensitizer agent described herein, applied to a wound, and photoactivated with a visible light source, e.g., an incandescent, fluorescent or mercury vapor light source, e.g., a xenon arc lamp, or a laser light source. The photochemical bandage can contain another beneficial material for wound healing, e.g., an antibiotic. In some embodiments, the photosensitizer-impregnated bandage, and/or the light source, can be supplied to a subject in a kit, e.g., a kit for use by a health care practitioner, or a kit for household use, which kits can contain instructions for use. The photochemical bandage described herein can be left on the wound, or can be replaced as necessary.

Such a bandage can be used ex-vivo, on a tissue removed from the body, or in situ on a subject, e.g., a human subject. For example, a bandage described herein can be used as an "artificial skin" or covering agent to cover large, oozing surfaces inside or outside the body. Burn patients, for example, could be covered with a photochemical bandage described herein to assist in preventing bacterial infection and to lessen the loss of body fluids and electrolytes through the burned areas.

The methods described herein can also be used to cross-link proteins for use in laboratory applications, e.g., to fix proteins for microscopy; to immobilize antibodies or other protein reagents to a substrate for diagnosis or purification; or to cross link proteins or peptides to a solid matrix for use in chromatographic or immunological applications.

KITS

The invention also includes kits for use in photochemical tissue bonding. Such kits can be used for laboratory or for clinical applications. Such kits include a photosensitizer agent, e.g., a photosensitizer described herein, and instructions for applying and irradiating the photosensitizer to cross-link at least one protein reagent for laboratory use, or to bond, repair, or heal an animal tissue, e.g., a human tissue, particularly in a human patient. The kits can include a container for storage, e.g., a light-protected and/or refrigerated container for storage of the photosensitizer agent. A photosensitizer included in the kits can be provided in various forms, e.g., in powdered, lyophilized, crystal, or liquid form. Optionally, a kit can include an additional agent for use in a tissue bonding, wound repair, or ocular therapy application, e.g., an antibiotic or a contact lens.

The kits described herein can also include a means to apply the photosensitizer agent to a tissue, for example, a syringe or syringe-like device, a dropper, a powder, an aerosol container, and/or a bandage material. In some embodiments, kits described herein which rely on photochemical mechanisms and reactive intermediate generation, e.g., singlet oxygen generation, can be stored in a high oxygen atmosphere.

Kits can include instructions for use, e.g., instructions for use in the absence of an exogenously supplied source of cross-linkable substrate, e.g., protein, e.g., fibrin or fibrinogen.

EXAMPLES

Example 1

Assessment of PTB in Repair of Corneal Incisions

PTB can be used to seal or repair a tissue, e.g., a wound, e.g., a corneal wound. This example illustrates the experimental procedure designed to test the efficacy of PTB, as described herein, using mammalian corneas ex vivo. Experiments were performed according to the following procedure.

Rabbit eyes were received on ice (Pel-Freez Biologicals) approximately 17-24 hours after sacrifice and enucleation. The eyes were kept on ice and used the same day. The eye to be studied was mounted on a plastic-covered polystyrene block and fixed in position by needles inserted through the extraocular muscles into the polystyrene. The eye was then placed under a dissecting microscope (Reichert Scientific Instruments, IL) allowing visualization of the treated area during the entire procedure. A 27 G needle was inserted parallel to the iris, 2 mm anterior to the limbus into clear cornea, and positioned above the lens in the anterior chamber. The needle was connected to both a blood pressure transducer (Harvard Apparatus, MA) and a mini-infuser 400 (Bard Harvard) via a T coupler. The pressure transducer consists of a transducer element that is hard wired to an amplifier box and uses a semi-disposable dome with an integral silicone rubber membrane. Pressure inside the dome is transmitted through the membrane to a plastic button whose motion is translated to a voltage. The voltage generated by the transducer amplifier combination is proportional to the lower limit of intraocular pressure (IOP). Signals from the transducer amplifier were recorded using a Macintosh G3 Power book equipped with a PCMICA (DAQCARD-1200) data acquisition card (National Instruments, TX). Data acquisition was controlled using programs written using the LabView 4 software package (National Instruments, TX). The voltage from the transducer and amplifier was converted to pressure by calibrating with a standing manometer.

Experiments on individual eyes were initiated by increasing the IOP to 30-40 mm Hg, using water infusion at a rate of 1 mL per minute. An incision was made in the cornea, 1 mm from the limbus and parallel to the iris, using a 3.5 mm angled keratome (Becton Dickinson Co.). For each eye the IOP required to produce fluid leakage from the incision ($IOP_L$) was recorded pre- and post-PTB treatment. A photosensitizer, dissolved in phosphate buffer solution (PBS, pH 7.2, Gibco BRL) was applied to the walls of the incision using a Gastight, 50 μl syringe (Hamilton Co.) with a 27 G needle. Confocal fluorescence spectroscopy confirmed the location of photosensitizer, e.g., rose Bengal, on the incision walls and indicated that the photosensitizer penetrated approximately 100 μM laterally into the wall of the incision.

The photosensitizers, their absorption maxima, and their absorption coefficients at the laser wavelength used in this Example were, e.g., rose bengal (RB), 550 nm, 33000 $dm^3$ $mol^{-1}$ $cm^{-1}$ at 514 nm; fluorescein (Fl), 490 nm, 88300 $dm^3$ $mol^{-1}$ $cm^{-1}$ at 488 nm; methylene blue (MB), 664 nm, 15600 $dm^3$ $mol^{-1}$ $cm^{-1}$ at 661 nm; riboflavin-5-phosphate (R-5-P), 445 nm, 4330 $dm^3$ $mol^{-1}$ $cm^{-1}$ at 488 nm; and N-hydroxy-pyridine-2-(1H)-thione (N-HPT), 314 nm, 2110 $dm^3$ $mol^{-1}$ $cm^{-1}$ at 351 nm. The photosensitizers were used as received with the exception of N-HPT which was recrystallized twice from aqueous ethanol before use. The concentrations of the photosensitizers were adjusted so that all the solutions had an absorbance of approximately 1.0 in a path length of 200 μm at the laser irradiation wavelength (with the exception of N-HPT for which the absorption was approximately a factor of 10 lower).

Figure 1:
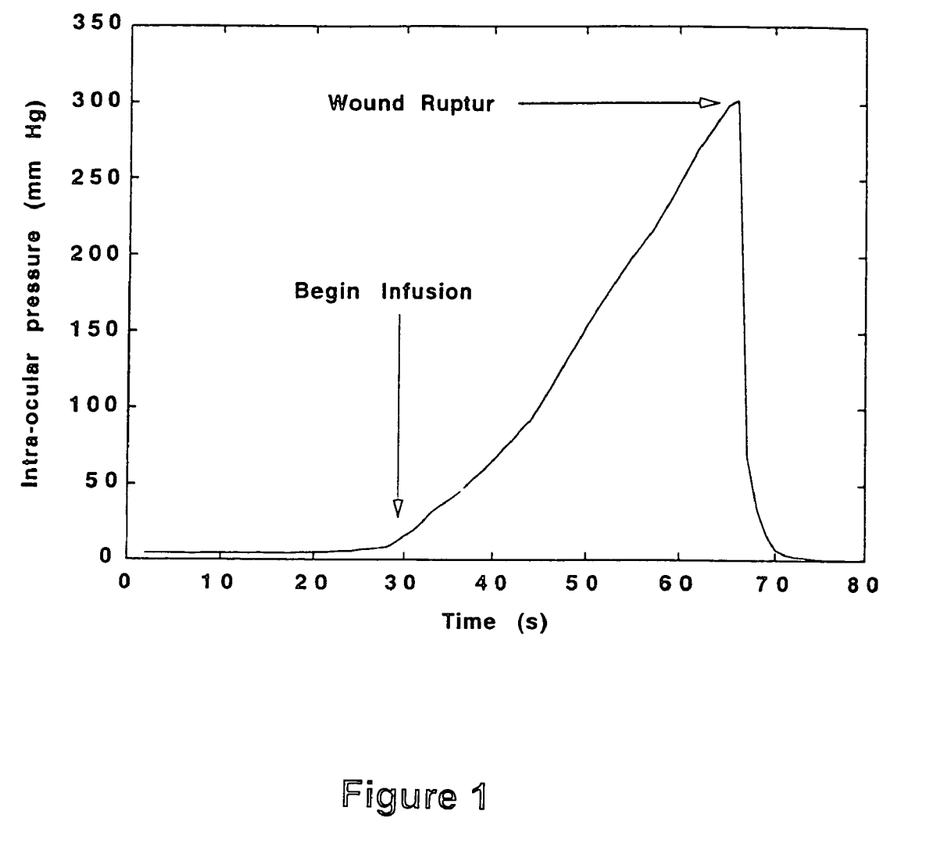
FIG. 1. Typical trace of increasing IOP with infusion time for a PTB treated eye showing IOPL at 300 mm Hg.

Irradiations employed a continuous wave (CW) argon-ion laser (Innova 100; Coherent, Inc., Palo Alto, Calif.) at 488 nm (for Fl and R-5-P), 514.5 nm (for RB) or 351 nm (for NHPT). An argon-ion-pumped dye laser (CR-599; Coherent) with 4-dicyanomethylene-2-methyl-6-(p-dimethylami-nostyryl)-4H-pyran dye (Exciton, Inc., Dayton, Ohio) was used for irradiation at 661 nm (for MB). Laser light was coupled into a 1 mm diameter quartz fiber and a 1 cm diameter spot on the tissue was created by using a combination of 1 and 2 inch focal length, S1-UV grade fused silica, biconvex lenses (Esco Products), mounted in a SM1 series cage assembly (Thorlabs, NJ). The 1 cm diameter circular spot was sufficient to cover the entire incision and the optics were adjusted so that the laser light was incident on the cornea at an angle approximately 45° to the plane of the incision. Dose response curves were obtained by varying the duration of the irradiation at a constant irradiance. In separate experiments the effects of laser irradiance were investigated by comparison of the same delivered dose using different irradiances. The doses used ranged from 124 to 1524 $J/cm^2$ and the irradiances used were 0.64, 1.27, 2.55 and 3.86 $W/cm^2$. The laser exposure time varied from 33 seconds for the lowest dose using the highest irradiance to 26 minutes, 27 seconds for the highest dose using the lowest irradiance. The $IOP_L$ was recorded immediately following treatment. Infusion was started (1 mL per minute) and the IOP increased until a maximum followed by a sharp decrease occurred, corresponding to the opening of the incision and leakage of fluid from the anterior chamber. A typical trace showing the changes in IOP with infusion time is shown in FIG. 1. Five to 10 rabbit eyes were tested for each condition of dose and irradiance.

Control experiments included: (1) irradiation with no photosensitizer application, (2) photosensitizer application only and (3) no photosensitizer or laser irradiation. In the experiments using no photosensitizer, PBS was applied to the incision walls, using the same method as described for the photosensitizers. In control experiments with no laser irradiation the eye was allowed to stand for the same period of time as the laser-treated samples.

Example 2

Use of Rose Bengal (RB) in PTB

In the cornea, RB can be used in PTB at a concentration of about 0.5 mM to 5 mM, preferably about 1 mM to 3 mM. The wavelength of irradiation for RB is preferably about 450-600 nm, more preferably about 500 to 560 nm. The dose of irradiation can be from about 0.5 to 2 kJ/cm$^2$. The irradiance delivered can be from about 0.2 to 3 W/cm$^2$. The duration of irradiation is preferably from about 1 to 10 minutes.

Figure 2:
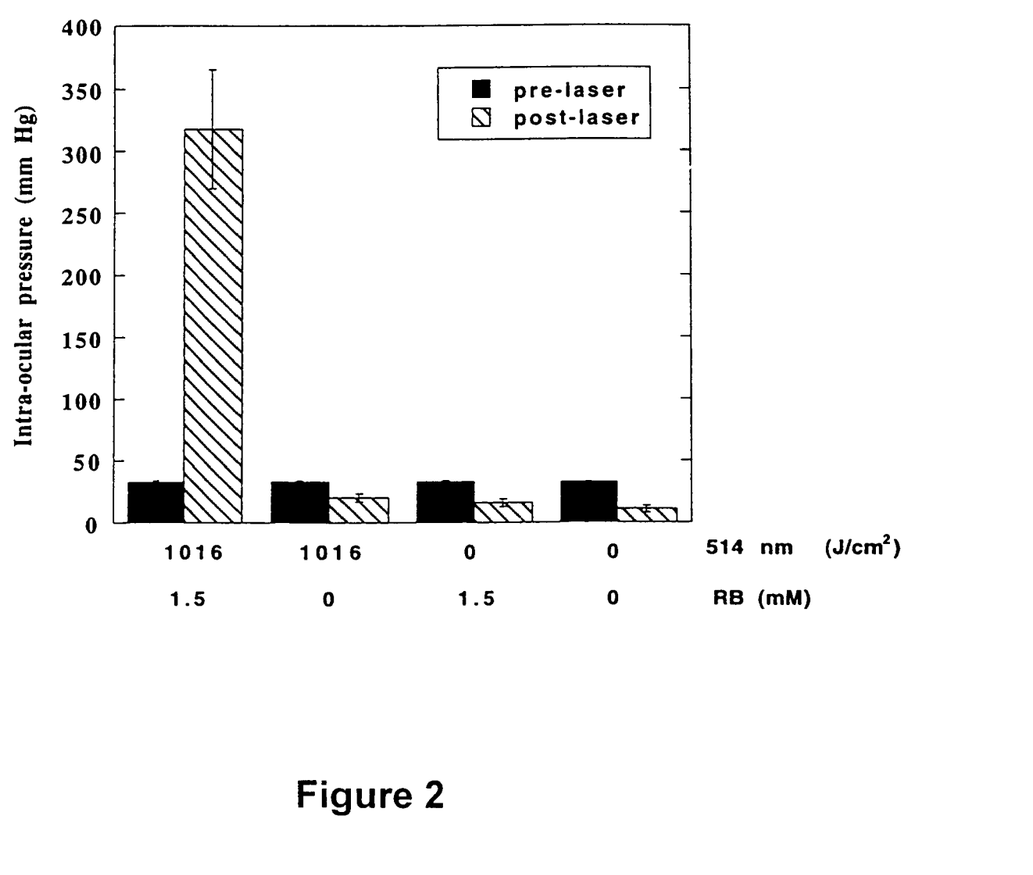
FIG. 2. Mean IOPL values for PTB treated eyes (n=5) using 514 nm light (2.55 $W/cm^2$) and RB (1.5 mM) in PBS. Additional controls are incisions treated with RB or buffer but no laser light.

Treatment of incisions with 1.5 mM RB and 514 nm laser light resulted in an increase in post-treatment IOP$_L$, as measured as described in Example 1. Control experiments demonstrated that a significant increase (p<0.005) in the IOP$_L$, following PTB treatment, occurred when both RB and laser irradiation were applied and not by either alone (FIG. 2). The mean IOP$_L$ of incisions treated with RB and 514 nm laser light was greater than 300+48 mm Hg, whereas laser irradiation alone or photosensitizer alone produced no significant increase between the pre- and post-treatment IOP$_L$ values.

Figure 3:
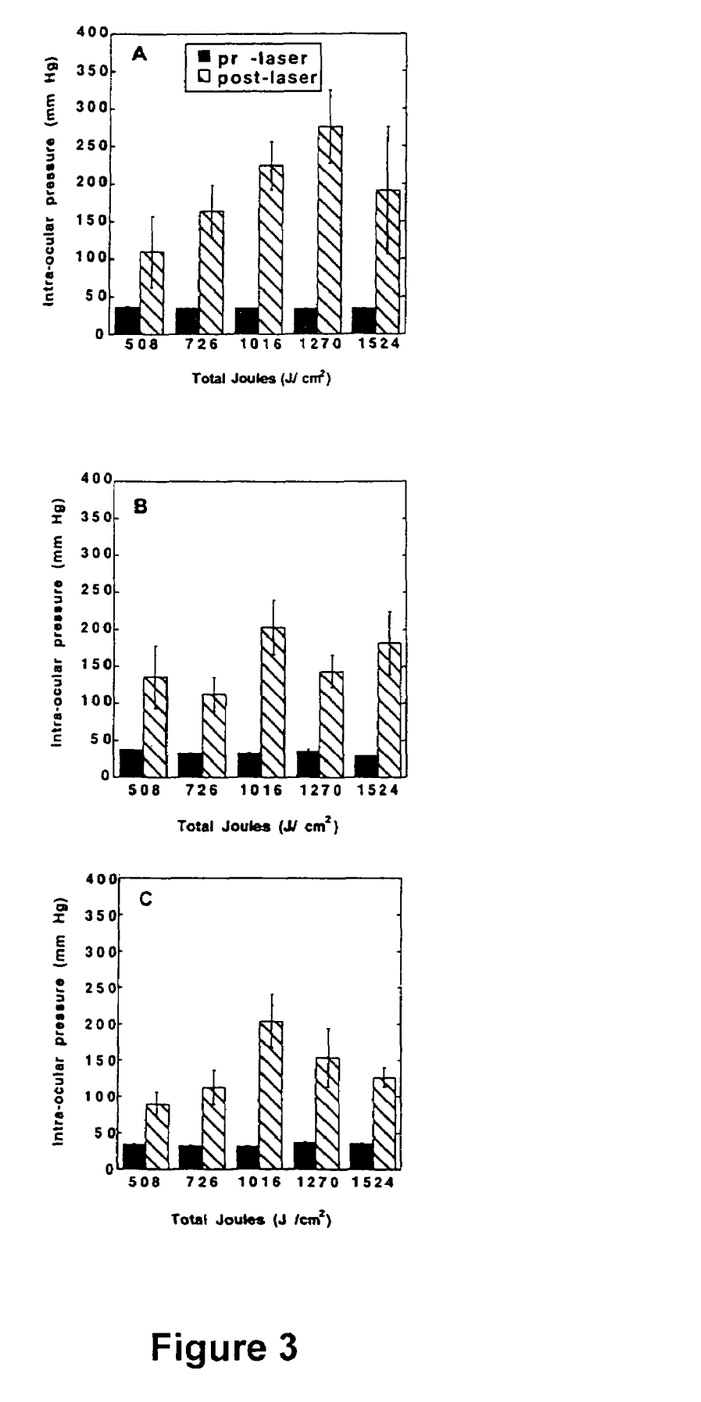
FIG. 3. Mean IOPL before and after PTB using RB and 514 nm irradiation. RB (10 µl, 1.5 mM) was applied to the incision surfaces then treated with the doses indicated using irradiances of: (A) 1.27 W/cm2, (B) 2.55 W/cm2 and (C) 3.82 W/cm2.

Dose response curves for IOP$_L$ are shown in FIG. 3 for RB doses delivered at irradiances of 1.27 (3A), 2.55 (3B) and 3.82 W/cm$^2$ (3C). A dose-response relationship was observed at the lowest irradiance (1.27 W/cm ) for doses between 508 and 1270 J/cm$^2$ (3A). No significant rise in the IOP$_L$ was observed for doses below 508 J/cm$^2$ at any irradiance tested. PTB was most efficient at 1270 J/cm$^2$ delivered at an irradiance of 1.27 W/cm . All doses delivered at the two lower irradiances (1.27 and 2.55 W/cm$^2$) gave IOP$_L$ values greater than 100 mm Hg. Treatment using irradiances of 2.55 and 3.82 W/cm$^2$ produced no obvious dose response pattern. In general, for a selected dose the IOP$_L$ was lower at higher irradiances. For example, at 1270 J/cm$^2$ the mean IOP$_L$ values were 274, 150 and 130 mm Hg for the irradiances 1.27 W/cm$^2$, 2.55 W/cm$^2$ and 3.86 W/cm$^2$.

Post-treatment, the eyes were examined for the presence of thermal damage. Tissue shrinkage and deformation around the wound site were taken as signs of thermal damage. Thermal damage to the cornea was not observed at the lowest irradiance tested (1.27 W/cm2). Thermal damage could be observed at doses of 762 to 1524 J/cm2 at the highest irradiance (3.82 W/cm2) and occasionally at 2.55 W/cm2. Thermal effects produced using high irradiances may produce collagen contraction resulting in distortion of the patient's vision.

Example 3

Use of Riboflavin-5-Phosphate (R-5-P) in PTB

In the cornea, R-5-P can be applied for PTB at a concentration of about 1 mM to 30 mM, preferably about 10 mM to 20 mM. The wavelength of irradiation for R-5-P is preferably about 400-600 nm, more preferably about 450 to 550 nm. The dose of irradiation can be from about 0.5 to 2 kJ/cm$^2$. The irradiance delivered can be from about 0.2 to 3 W/cm$^2$. The duration of irradiation is preferably from about 1 to 10 minutes.

Figure 4:
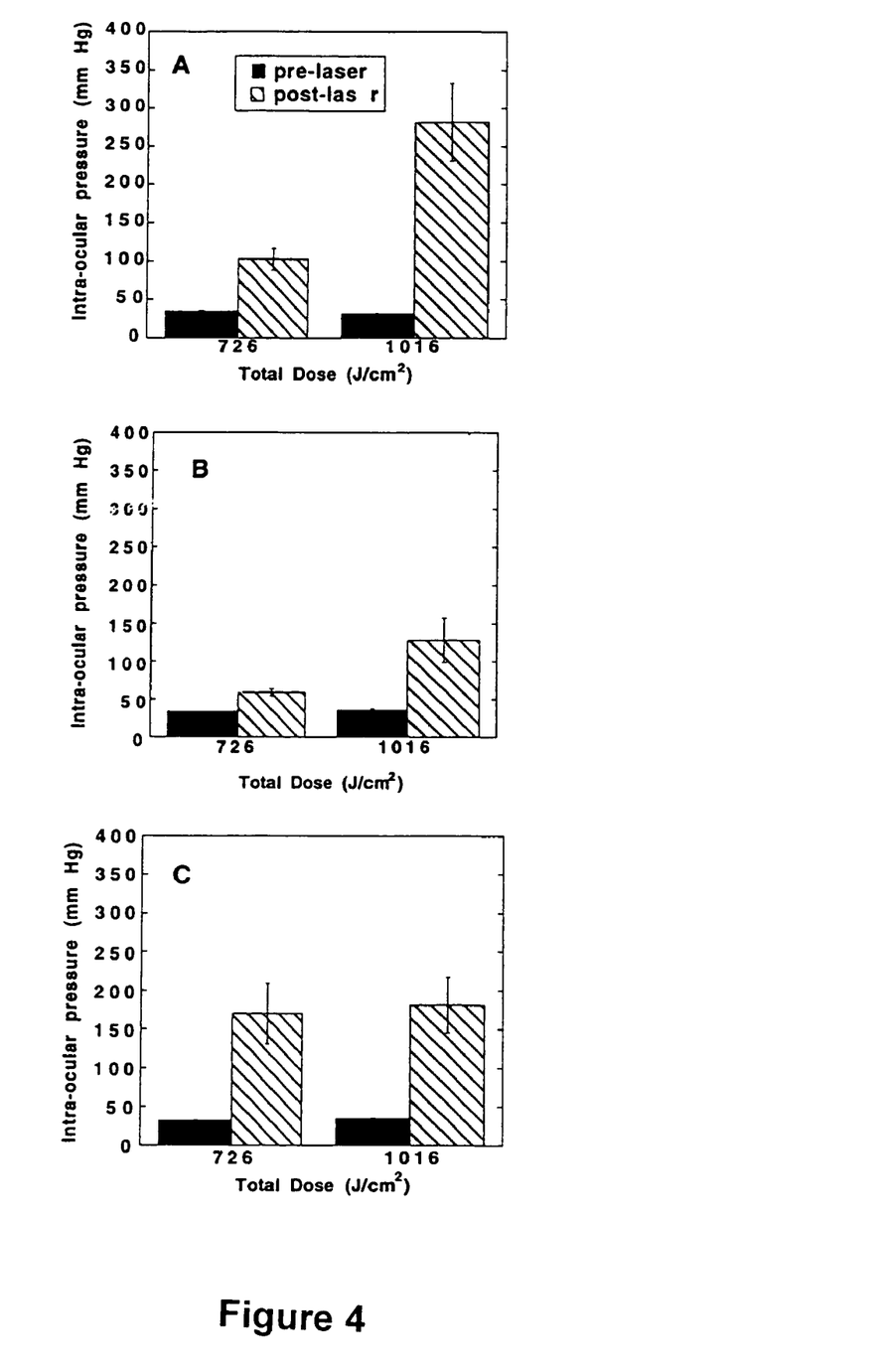
FIG. 4. Mean IOPL before and after PTB using R-5-P and 488 nm irradiation. R-5-P (40 µl, 11 mM) was applied to the incision surfaces then treated with the doses indicated using irradiances of: (A) 1.27 W/cm2, (B) 2.55 W/cm2 and (C) 3.82 W/cm2.

The effect of R-5-P PTB was assessed as described in Example 1. The application of 11 mM R-5-P and irradiation using 488 nm light, at the same irradiances used for RB, and doses of 762 J/cm$^2$ and 1016 J/cm$^2$, significantly increased the post PTB treatment IOP$_L$ value (p<0.05), see FIG. 4. The IOP$_L$ values observed using R-5-P are of a similar magnitude to those for RB. However, the IOP$_L$ values observed for each dye at the same irradiance and dose were not comparable. Although the treatment produces significant increases in IOP$_L$, no simple pattern between the two dyes is observed.

Example 4

Use of N-hydroxypyridine-2-(1H)-thione (N-HTP) in PTB

In the cornea, N-HTP can be applied at a concentration of about 0.5 mM to 10 mM, preferably about 3 mM to 6 mM. The wavelength of irradiation for N-HTP is preferably about 330-400 nm. The dose of irradiation can be from about 0.5 to 2 kJ/cm$^2$. The irradiance delivered can be from about 0.2 to 3 W/cm$^2$. The duration of irradiation is preferably from about 1 to 10 minutes. A 4.5 mM solution of NHPT was applied to the walls of the incision, as described in Example 1, and irradiated using 351 nm light (0.64 W/cm2) at doses ranging from 127 J/cm2 to 508 J/cm2. Mean IOPL values of 60±23 mm Hg and 126±40 mm Hg were produced when using the doses of 254 J/cm2 and 508 J/cm2 respectively, lower doses than used for the other photosensitizers.

Example 5

Use of Methylene Blue (MB) in PTB

MB is a frequently used dye in ophthalmic surgery that has been reported to photosensitize collagen cross-links in rat tail tendon (Ramshaw et al. (1994) *Biochim Biophys Acta* 1206:225-230). Our previous studies showed that MB and 355 nm light did not produce efficient cross-linking of soluble collagen. MB was therefore used as a control in these ex vivo studies. MB (3 mM) was applied to the walls of the incision, as described in Example 1, and irradiated with 0.64 W/cm$^2$ of 661 nm light. Doses of 508/cm$^2$, 762 J/cm$^2$ and 1016 J/cm$^2$ did not increase the post-treatment, IOP$_L$. However, it was observed that MB did not stain the corneal tissue efficiently, which perhaps explains its low efficiency for PTB.

Example 6

Assessment of Thermal Contribution to PTB

Laser activated tissue welding has been studied in a variety of tissues (Abergel et al. (1986) *J Am Acad Dermatol* 14: 810-814; Cilesiz et al., supra; Massicotte et al. (1998) *Lasers in Surgery and Medicine* 23:18-24; Oz et al. (1990) *J Vasc Surg.* 11:718-725; Poppas et al. (1996) *Lasers in Surgery and Medicine* 18:335-344; Poppas et al. (1996) *Lasers in Surgery and Medicine* 19: 360-368; Stewart et al. (1996) *Lasers in Surgery and Medicine* 19:9-16; Wider et al. (1991) *Plastic Reconstr Surg* 88:1018-1025). In tissue welding, the laser radiation is used to heat the tissue to temperatures at which collagen denatures and, upon cooling, the collagen molecules intertwine to form a 'weld'. Additionally, dye-enhanced thermal welding has been investigated (Bass & Treat (1995) *Lasers Surg and Med* 17: 315-349; Chuck et al. (1989) *Lasers Surg and Med* 9:471-477). In this method the dye selectively absorbs the laser energy and then releases heat to the desired area, reducing peripheral tissue damage. These methods, however, are not appropriate for the cornea due to the potential reduction in visual acuity that would result from the corneal deformation produced by thermal tissue damage. When performing PTB on the cornea, heating must be avoided.

Figure 5:
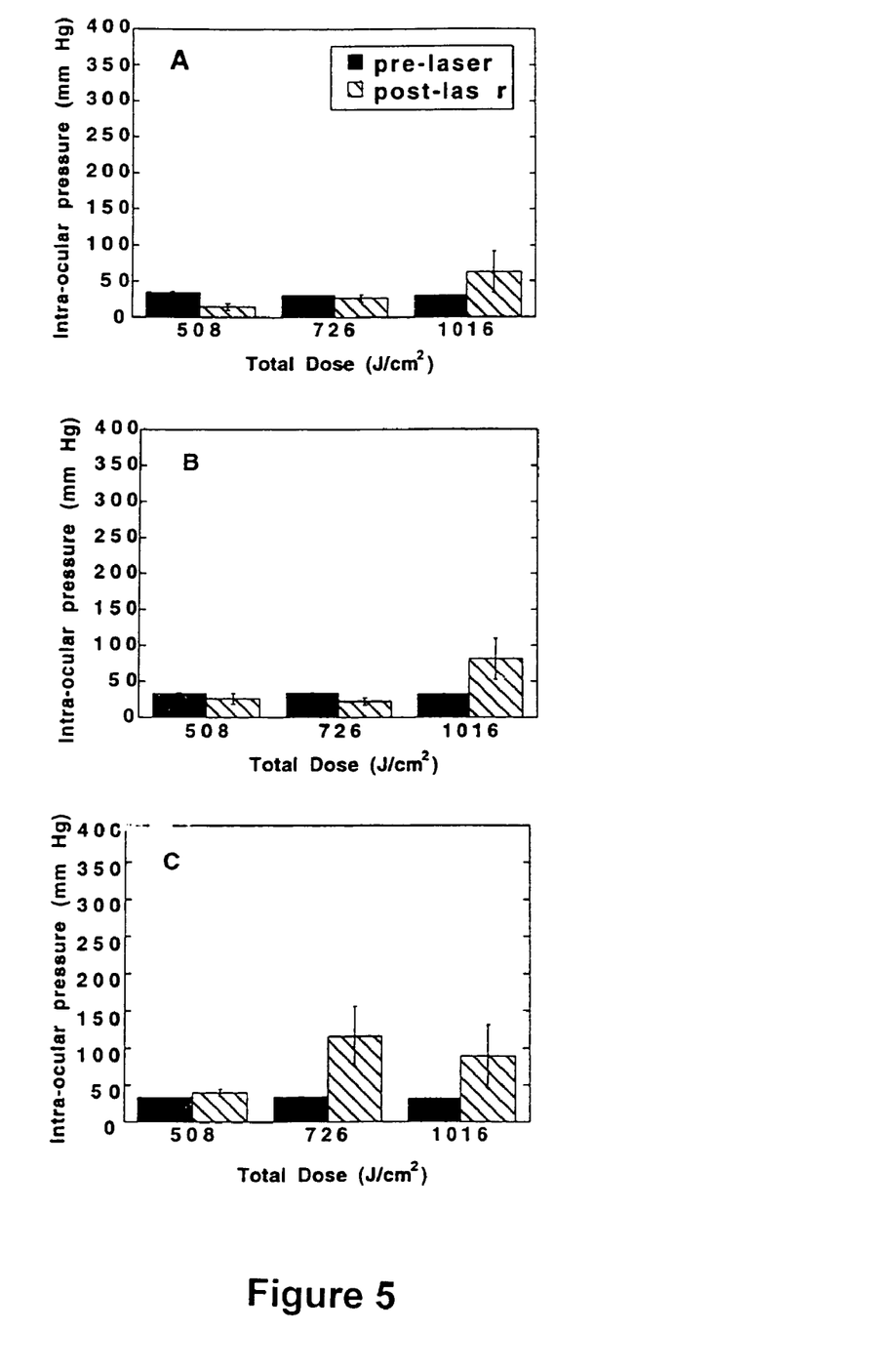
FIG. 5. Mean IOPL values before and after PTB using Fl and 488 nm irradiation. Fl (40 µl, 0.6 mM) was applied to the incision surfaces then treated with the doses indicated using irradiances of: (A) 1.27 W/cm2, (B) 2.55 W/cm2 and (C) 3.82 W/cm2.

We evaluated the possibility that non-photochemical processes contribute to wound closure by comparing PTB produced by RB with that produced by fluorescein (Fl), a dye with a similar structure but which is not expected to induce protein cross-links. RB and Fl are both xanthene dyes. However, RB is halogenated (4 iodines and 4 chlorines) and the presence of these heavy atoms causes RB to be photochemically active (Lessing et al. (1982) *J Mol Struct* 84:281-292). Fl has a high quantum yield of fluorescence and lower quantum yield of triplet state formation than RB (Fleming et al. (1977) *JACS* 99:4306-4311) and will, therefore, produce a lower proportion of active species with the potential to produce collagen cross-links. A solution of 0.6 mM Fl was applied and irradiated using 488 nm laser light at the same range of irradiances used for RB and at doses from 508 J/cm$^2$ to 1016 J/cm$^2$ (FIG. 5). No increase in IOP$_L$ was observed for the incisions treated with the two lowest doses using the two lowest irradiances studied. However, at the highest dose for all irradiances an increase IOP$_L$ values was observed with values ranging from 63±30 to 89±42 mm Hg although this is much less efficient than RB (compare FIGS. 3 and 5). These results suggest that PTB is indeed produced by photochemical processes. The IOP$_L$ value of 116±40 mm Hg obtained using a dose of 762 J/cm$^2$ at 3.82 W/cm$^2$ (laser exposure time of 3 min, 10 sec) is considerably higher than any other observed using Fl. The sealing observed at the highest irradiance (3.82 W/cm$^2$) and dose (762 J/cm$^2$) suggests that some other effect is operating, such as a thermal mechanism under these high irradiance conditions.

Example 7

PTB versus Sutures

The IOP$_L$ following PTB treatment, as described in Example 1, was compared to that obtained using sutures. Two interrupted radial sutures of black monofilament 10-0 nylon (Ethilon Inc.) were used to close the keratome incision. The sutures were placed in a radial fashion at approximately 90% corneal depth. IOP$_L$ values with sutures were approximately 230 mm Hg. This value is similar for the incisions closed with PTB treatment.

Example 8

In vivo PTB

PTB was performed in vivo in New Zealand rabbits to repair two types of corneal wounds.

In group I, 3.5-mm incisions were performed in 20 rabbit (New Zealand White) corneas. Dose and laser irradiance were varied in subgroups of five or more eyes for each condition and appropriate control eyes. Photoactivation was performed with a 514 nm Argon Laser. Wound leak and incisional bursting pressure of the treated and untreated rabbit eyes was determined in vivo, with the animals under anesthetic.

Group I wounds were healed using, e.g., 191 J/cm2, applying 1.5 mM RB. The immediate in vivo bursting pressure was 495±10 mm Hg for PTB treated eyes. Under the same conditions the values of the busting pressure in the control eye varied from 15 to 60 mm Hg. One day after surgery, the bursting pressure was the same for PTB treated eyes and control eyes (approximately 450±125 mmHg). At 14 days, the bursting pressure exceeded 500 mm Hg in both PTB-treated and control eyes.

In Group II, 6-mm Penetrating Keratoplasy (PK) incisions anchored by 4-16 sutures were performed in 16 rabbit corneas. Half of the corneas in each group underwent PTB where 1% Rose Bengal dye was applied to the wound edges followed by laser irradiation at fluence of 191 J/cm2. Photoactivation was performed with a 514 nm Argon Laser and a 532-nm CW Nd: YAG laser. Wound leak and incisional bursting pressure were determined in vivo in the immediate postoperative period. PTB-treated eyes showed an immediate bursting pressure of 410±70 mm Hg for the PTB-treated eyes, compared to 250±150 mm Hg for the control eyes with sutures alone. This result indicate that PTB is useful and effective as a supplement to sutures, as well as on its own.

The results described herein show that PTB is effective to seal, close, or heal a tissue, e.g., a corneal incision, in vivo, in a subject, e.g, an animal, or a human. The presence of a protein, e.g., a protein based sealant, e.g., fibrinogen, is not necessary to obtain a good tissue seal. PTB may be used instead of, or in addition to, other wound healing techniques, e.g., sutures.

A number of embodiments of the invention have been described. Nevertheless, it will be understood that various modifications may be made without departing from the spirit and scope of the invention. Accordingly, other embodiments are within the scope of the following claims.

We claim:

1. A method for tissue repair, comprising:
   contacting a tissue in need of repair, and optionally a second tissue, with at least one photosensitizer agent to form a tissue-photosensitizer mixture; and
   applying electromagnetic energy at a wavelength of at least 488 nm and at an irradiance less than 3.5 W/cm$^2$ to the tissue-photosensitizer mixture in a manner effective to produce cross linking of a protein in the tissue without producing substantial thermal damage,
   wherein the tissue is not contacted with an exogenous cross-linkable substrate which is cross linked by the application of electromagnetic energy,
   thereby creating a tissue seal that repairs the tissue, wherein the repaired tissue has tensile strength.

2. The method of claim 1, wherein the tissue is corneal tissue.

3. The method of claim 1, wherein at least one photosensitizer agent is selected from the group consisting of Rose Bengal, and riboflavin-5-phosphate.

4. The method of claim 1, wherein at least one photosensitizer agent is Rose Bengal.

5. The method of claim 1, wherein the contacting step occurs ex vivo.

6. The method of claim 1, wherein the contacting step occurs in vivo in a subject.

7. The method of claim 6, wherein the subject is a human.

8. The method of claim 1, wherein the application of electromagnetic energy to the tissue-photosensitizer mixture occurs without more than a 3° C. rise in temperature.

9. The method of claim 1, wherein the application of electromagnetic energy to the tissue-photosensitizer mixture occurs without more than a 2° C. rise in temperature.

10. The method of claim 1, wherein the application of electromagnetic energy to the tissue-photosensitizer mixture occurs without more than a 1° C. rise in temperature.

11. The method of claim 1, wherein at least one photosensitizer agent is a thiazine dye.

12. The method of claim 1 wherein the electromagnetic energy is applied for at least five minutes.

13. A method for repairing a corneal lesion, comprising:
   contacting a lesion in corneal tissue with at least one photosensitizer agent to form a corneal tissue-photosensitizer mixture; and
   applying electromagnetic energy having a wavelength of at least 488 nm and at an irradiance less than 3.5 W/cm$^2$ to the corneal tissue-photosensitizer mixture in a manner effective to elicit the production of a reactive species from the photosensitizer without producing substantial thermal damage, wherein the corneal tissue is not contacted with an exogenous cross-linkable substrate which is cross-linked by the application of electromagnetic energy, thereby promoting a partial or complete repair of the corneal lesion, such that the intraocular pressure limit of the repaired corneal lesion is greater than 100 mm Hg.

14. The method of claim 13, wherein the corneal lesion is caused by a surgical procedure.

15. The method of claim 14, wherein the surgical procedure is selected from the group consisting of corneal transplant surgery, cataract surgery, laser surgery, keratoplasty, refractive surgery, cornea reshaping, and treatment of corneal laceration.

16. The method of claim 13, wherein the electromagnetic energy applied is about 124 to about 762 J/cm$^2$.

17. The method of claim 13, wherein the electromagnetic energy is applied at an irradiance less than 3.5 W/cm$^2$.

18. The method of claim 13 wherein the electromagnetic energy is applied for at least five minutes.

19. A method for repairing a corneal lesion in vivo in a living subject, comprising:

contacting a lesion in corneal tissue with Rose Bengal (RB) to form a corneal tissue-RB mixture; and applying electromagnetic energy at an irradiance less than 3.5 W/cm$^2$ to the corneal tissue-RB mixture in a manner effective to elicit the production of a reactive species from the RB without producing substantial thermal damage, wherein the corneal tissue is not contacted with an exogenous cross-linkable substrate which is cross-linked by the application of electromagnetic energy, thereby promoting a partial or complete repair of the corneal lesion, such that the intraocular pressure limit of the repaired corneal lesion is greater than 100 mm Hg.

20. The method of claim 19, wherein the subject is a human.

21. The method of claim 19, wherein the corneal lesion is caused by a surgical procedure.

22. The method of claim 21, wherein the surgical procedure is selected from the group consisting of corneal transplant surgery, cataract surgery, laser surgery, keratoplasty, refractive surgery, cornea reshaping, and treatment of corneal laceration.

23. A method for creating a tissue seal, comprising:

contacting a tissue in need of repair, and optionally a second tissue, with at least one photosensitizer agent to form a tissue-photosensitizer mixture; and applying electromagnetic energy at a wavelength of at least 488 nm and at an irradiance less than 3.5 W/cm$^2$ to the tissue-photosensitizer mixture in a manner effective to produce cross linking of a protein in the tissue without producing substantial thermal damage, wherein the tissue is not contacted with an exogenous cross-linkable substrate which is cross linked by the application of electromagnetic energy, thereby creating a tissue seal, wherein the pressure limit of the tissue seal is greater than 100 mm Hg.

* * * * *

UNITED STATES PATENT AND TRADEMARK OFFICE
CERTIFICATE OF CORRECTION

| | | |
|---|---|---|
| PATENT NO. | : 7,331,350 B2 | Page 1 of 1 |
| APPLICATION NO. | : 09/781577 | |
| DATED | : February 19, 2008 | |
| INVENTOR(S) | : Irene E. Kochevar et al. | |

It is certified that error appears in the above-identified patent and that said Letters Patent is hereby corrected as shown below:

Column 1, line 9, immediately before the heading "BACKGROUND," please add the following new heading and paragraph:

--STATEMENT REGARDING FEDERALLY SPONSORED RESEARCH OR DEVELOPMENT

This invention was made with Government support under Grant Nos. F49620-01-1-0014, N00014-96-1-0927, DAMD17-02-2-0006, and DE-FG02-91ER61228 awarded by the U.S. Department of the Air Force, the U.S. Department of the Navy, the U.S. Department of the Army, and the U.S. Department of Energy. The Government has certain rights in this invention.--

Signed and Sealed this

Twenty-eighth Day of July, 2009

JOHN DOLL
*Acting Director of the United States Patent and Trademark Office*